(12) United States Patent
Stashenko et al.

(10) Patent No.: US 6,777,537 B1
(45) Date of Patent: Aug. 17, 2004

(54) OSTEOCLAST PROTON PUMP SUBUNIT

(75) Inventors: Philip Stashenko, Norfolk, MA (US); Yi-Ping Li, Boston, MA (US)

(73) Assignee: Forsyth Dental Infirmary for Children, Boston, MA (US)

(*) Notice: Subject to any disclaimer, the term of this patent is extended or adjusted under 35 U.S.C. 154(b) by 33 days.

(21) Appl. No.: 09/618,304

(22) Filed: Jul. 18, 2000

Related U.S. Application Data

(63) Continuation of application No. 08/605,378, filed on Feb. 22, 1996, now abandoned.

(51) Int. Cl.[7] .............................................. C07K 14/435
(52) U.S. Cl. ...................................................... 530/350
(58) Field of Search .......................... 530/350; 435/69.1

(56) References Cited

FOREIGN PATENT DOCUMENTS

| WO | WO94/23033 | 10/1994 |
|---|---|---|
| WO | WO 01/94629 A2 * | 12/2001 |

OTHER PUBLICATIONS

Ngo et al., 1994, The Protein Folding Problem and Tertiary Structure Prediction, Merz et al., eds., Birkhauser, Boston, pp. 491–495.*

Wells, 1990, Biochemistry 29:8509–8517.*

Li, Y–P. et al., "Molecular Cloning and Characterization of a Putative Novel Human Osteoclast–Specific 116–kDa Vacuolar Proton Pump Subunit", *Biochemical and Biophysical Research Communications*, 218:813–821 (1996).

Shapiro, L.H. et al., "Carbonic Anhydrase II is Induced in HL–60 Cells by 1,25–Dihydroxyvitamin $D_3$: a Model for Osteoclast Gene Regulation", *FEBS Letters*, 249 (2) : 307–310 (1989).

Ketcham, C.M. et al., "Molecular Cloning of the Type 5, Iron–Containing, Tartrate–Resistant Acid Phosphatase from Human Placenta", *The Journal of Biological Chemistry*, 264 (1) :557–563 (1989).

Wilhelm, S.M. et al., "SV40–Transformed Human Lung Fibroblasts Secrete a 92–kDa Type IV Collagenase Which Is Identical to That Secreted by Normal Human Macrophages", *The Journal of Biological Chemistry*, 264 (29) : 17213–17221 (1989).

Ek–Rylander, B. et al., "Cloning, Sequence, and Developmental Expression of a Type 5, Tartrate–Resistant, Acid Phosphatase of Rat Bone", *The Journal of Biological Chemistry*, 266 (36) :24684–24689 (1991).

Tezuka, K. et al., "Molecular Cloning of a Possible Cysteine Proteinase Predominatly Expressed in Osteoclasts", *The Journal of Biological Chemistry*, 269 (2) :1106–1109 (1994).

Tezuka, K. et al., "Identification of Osteopontin in Isolated Rabbit Osteoclasts", *Biochemical and Biophysical Research Communications*, 186 (2) :911–917 (1992).

Peng, S.–B. et al., "Alternative mRNA Splicing Generates Tissue–specific Isoforms of 116–kDA Polypeptide of Vacuolar Proton Pump," *J. of Biol Chem.* 269 (25) :17262–17266 (1994).

Crider, B.P. et al., "Bafilomycin Inhibits Proton Flow Through the $H^+$ Channel of Vacuolar Proton Pumps," *J. of Biol. Chem.* 269 (26) : 17379–17381 (1994).

Perlin, M.S. et al., "Structure of the 116–kDA Polypeptide of the Clathrin–coated Vesicle/Synaptic Vesicle Proton Pump," *J. of Biol. Chem.* 266 (6) :3877–3991 (1991).

Li, Y.–P. et al., "Atp6i–deficient Mice Exhibit Severe Osteoporosis Due to Loss of Osteoclast–mediated Extracellular Acidification," *Nat. Genet.*, 23:447–51 (1999).

Mattsson, J.P., et al., "Isolation and Reconstitution of a Vacuolar–type Proton Pump of Osteoclast Membranes", *J. Biol. Chem.*, 269 (40) :24979–24982 (1994).

* cited by examiner

*Primary Examiner*—Elizabeth Kemmerer
(74) *Attorney, Agent, or Firm*—Ingrid A. Beattie; Mintz, Levin, Cohn, Ferris, Glovsky and Popeo, P.C.

(57) ABSTRACT

Novel gene encoding a human 116-kDa osteoclast proton pump subunit and the protein encoded thereby. Methods of treatment of bone mass disorders utilizing said gene, and antibodies that bind to the protein encoded by said gene.

2 Claims, 3 Drawing Sheets

```
CGGCGTGCGCGGACGGGCAGCCAGCAGCGGAGGCGCGGCGCAGCACACCCGGGGACCATG  60
                                                           M   1
GGCTCCATGTTCCGGAGCGAGGAGGTGGCCCTGGTCCAGCTCTTTCTGCCCACAGCGGCT 120
 G  S  M  F  R  S  E  E  V  A  L  V  Q  L  F  L  P  T  A  A  21
GCCTACACCTGCGTGAGTCGGCTGGGCGAGCTGGGCCTCGTGGAGTTCAGAGACCTCAAC 180
 A  Y  T  C  V  S  R  L  G  E  L  G  L  V  E  F  R  D  L  N  41
GCCTCGGTGAGCGCCTTCCAGAGACGCTTTGTGGTTGATGTTTGGCGCTGTGAGGAGCTG 240
 A  S  V  S  A  F  Q  R  R  F  V  V  D  V  W  R  C  E  E  L  61
GAGAAGACCTTCACCTTCCTGCAGGAGGAGGTGCGGCGGGCTGGGCTGGTCCTGCCCCCG 300
 E  K  T  F  T  F  L  Q  E  E  V  R  R  A  G  L  V  L  P  P  81
CCAAAGGGGAGGCTGCCGGCACCCCCACCCCGGGACCTGCTGCGCATCCAGGAGGAGACG 360
 P  K  G  R  L  P  A  P  P  P  R  D  L  L  R  I  Q  E  E  T  101
GAGCGCCTGGCCCAGGAGCTGCGGGATGTGCGGGGCAACCAGCAGGCCCTGCGGGCCCAG 420
 E  R  L  A  Q  E  L  R  D  V  R  G  N  Q  Q  A  L  R  A  Q  121
CTGCACCAGCTGCAGCTCCACGCCGCCGTGCTACGCCAGGGCCATGAACCTCAGCTGGCA 480
 L  H  Q  L  Q  L  H  A  A  V  L  R  Q  G  H  E  P  Q  L  A  141
GCCGCCCACACAGATGGGGCCTCAGAGAGGACGCCCCTGCTCCAGGCCCCCGGGGGGCCG 540
 A  A  H  T  D  G  A  S  E  R  T  P  L  L  Q  A  P  G  G  P  161
CACCAGGACCTGAGGGTCAACTTTGTGGCAGGTGCCGTGGAGCCCCACAAGGCCCCTGCC 600
 H  Q  D  L  R  V  N  F  V  A  G  A  V  E  P  H  K  A  P  A  181
CTAGAGCGCCTGCTCTGGAGGGCCTGCCGCGGCTTCCTCATTGCCAGCTTCAGGGAGCTG 660
 L  E  R  L  L  W  R  A  C  R  G  F  L  I  A  S  F  R  E  L  201
GAGCAGCCGCTGGAGCACCCCGTGACGGGCGAGCCAGCCACGTGGATGACCTTCCTCATC 720
 E  Q  P  L  E  H  P  V  T  G  E  P  A  T  W  M  T  F  L  I  221
TCCTACTGGGGTGAGCAGATCGGACAGAAGATCCGCAAGATCACGGACTGCTTCCACTGC 780
 S  Y  W  G  E  Q  I  G  Q  K  I  R  K  I  T  D  C  F  H  C  241
CACGTCTTCCCGTTTCTGCAGCAGGAGGAGGCCCGCCTCGGGGCCCTGCAGCAGCTGCAA 840
 H  V  F  P  F  L  Q  Q  E  E  A  R  L  G  A  L  Q  Q  L  Q  261
CAGCAGAGCCAGGAGCTGCAGGAGGTCCTCGGGGAGACAGAGCGGTTCCTGAGCCAGGTG 900
 Q  Q  S  Q  E  L  Q  E  V  L  G  E  T  E  R  F  L  S  Q  V  281
CTAGGCCGGGTGCTGCAGCTGCTGCCGCCAGGGCAGGTGCAGGTCCACAAGATGAAGGCC 960
 L  G  R  V  L  Q  L  L  P  P  G  Q  V  Q  V  H  K  M  K  A  301
GTGTACCTGGCCCTGAACCAGTGCAGCGTGAGCACCACGCACAAGTGCCTCATTGCCGAG 1020
 V  Y  L  A  L  N  Q  C  S  V  S  T  T  H  K  C  L  I  A  E  321
GCCTGGTGCTCTGTGCGAGACCTGCCCGCCCTGCAGGAGGCCCTGCGGGACAGCTCGATG 1080
 A  W  C  S  V  R  D  L  P  A  L  Q  E  A  L  R  D  S  S  M  341
GAGGAGGGAGTGAGTGCCGTGGCTCACCGCATCCCCTGCCGGGACATGCCCCCCACACTC 1140
 E  E  G  V  S  A  V  A  H  R  I  P  C  R  D  M  P  P  T  L  361
ATCCGCACCAACCGCTTCACGGCCAGCTTCCAGGGCATCGTGGATCGCTACGGCGTGGGC 1200
 I  R  T  N  R  F  T  A  S  F  Q  G  I  V  D  R  Y  G  V  G  381
CGCTACCAGGAGGTCAACCCCGCTCCCTACACCATCATCACCTTCCCCTTCCTGTTTGCT 1260
 R  Y  Q  E  V  N  P  A  P  Y  T  I  I  T  F  P  F  L  F  A  401
```

FIGURE 1A

```
GTGATGTTCGGGGATGTGGGCCACGGGCTGCTCATGTTCCTCTTCGCCCTGGCCATGGTC 1320
 V  M  F  G  D  V  G  H  G  L  L  M  F  L  F  A  L  A  M  V  421
CTTGCGGAGAACCGACCGGCTGTGAAAGCCGCGCAGAACGAGATCTGGCAGACTTTCTTC 1380
 L  A  E  N  R  P  A  V  K  A  A  Q  N  E  I  W  Q  T  F  F  441
AGGGGCCGCTACCTGCTCCTGCTTATGGGCCTGTTCTCCATCTACACCGGCTTCATCTAC 1440
 R  G  R  Y  L  L  L  M  G  L  F  S  I  Y  T  G  F  I  Y     461
AACGAGTGCTTCAGTCGCGCCACCAGCATCTTCCCCTCGGGCTGGAGTGTGGCCGCCATG 1500
 N  E  C  F  S  R  A  T  S  I  F  P  S  G  W  S  V  A  A  M  481
GCCAACCAGTCTGGCTGGAGTGATGCATTCCTGGCCCAGCACACGATGCTTACCCTGGAT 1560
 A  N  Q  S  G  W  S  D  A  F  L  A  Q  H  T  M  L  T  L  D  501
CCCAACGTCACCGGTGTCTTCCTGGGACCCTACCCCTTTGGCATCGATCCTATTTGGAGC 1620
 P  N  V  T  G  V  F  L  G  P  Y  P  F  G  I  D  P  I  W  S  521
CTGGCTGCCAACCACTTGAGCTTCCTCAACTCCTTCAAGATGAAGATGTCCGTCATCCTG 1680
 L  A  A  N  H  L  S  F  L  N  S  F  K  M  K  M  S  V  I  L  541
GGCGTCGTGCACATGGCCTTTGGGGTGGTCCTCGGAGTCTTCAACCACGTGCACTTTGGC 1740
 G  V  V  H  M  A  F  G  V  V  L  G  V  F  N  H  V  H  F  G  561
CAGAGGCACCGGCTGCTGCTGGAGACGCTGCCGGAGCTCACCTTCCTGCTGGGACTCTTC 1800
 Q  R  H  R  L  L  L  E  T  L  P  E  L  T  F  L  L  G  L  F  581
GGTTACCTCGTGTTCCTAGTCATCTACAAGTGGCTGTGTGTCTGGGCTGCCAGGGCCGCC 1860
 G  Y  L  V  F  L  V  I  Y  K  W  L  C  V  W  A  A  R  A  A  601
TCGCCCAGCATCCTCATCCACTTCATCAACATGTTCCTCTTCTCCCACAGCCCCAGCAAC 1920
 S  P  S  I  L  I  H  F  I  N  M  F  L  F  S  H  S  P  S  N  621
AGGCTGCTCTACCCCCGGCAGGAGGTGGTCCAGGCCACGCTGGTGGTCCTGGCCTTGGCC 1980
 R  L  L  Y  P  R  Q  E  V  V  Q  A  T  L  V  V  L  A  L  A  641
ATGGTGCCCATCCTGCTGCTTGGCACACCCCTGCACCTGCTGCACCGCCACCGCCGCCGC 2040
 M  V  P  I  L  L  L  G  T  P  L  H  L  L  H  R  H  R  R  R  661
CTGCGGAGGAGGCCCGCTGACCGACAGGAGGAAAACAAGGCCGGGTTGCTGGACCTGCCT 2100
 L  R  R  R  P  A  D  R  Q  E  E  N  K  A  G  L  L  D  L  P  681
GACGCATCTGTGAATGGCTGGAGCTCCGATGAGGAAAAGGCAGGGGGCCTGGATGATGAA 2160
 D  A  S  V  N  G  W  S  S  D  E  E  K  A  G  G  L  D  D  E  701
GAGGAGGCCGAGCTCGTCCCCTCCGAGGTGCTCATGCACCAGGCCATCCACACCATCGAG 2220
 E  E  A  E  L  V  P  S  E  V  L  M  H  Q  A  I  H  T  I  E  721
TTCTGCCTGGGCTGCGTCTCCAACACCGCCTCCTACCTGCGCCTGTGGGCCCTGAGCCTG 2280
 F  C  L  G  C  V  S  N  T  A  S  Y  L  R  L  W  A  L  S  L  741
GCCCACGCCCAGCTGTCCGAGGTTCTGTGGGCCATGGTGATGCGCATAGGCCTGGGCCTG 2340
 A  H  A  Q  L  S  E  V  L  W  A  M  V  M  R  I  G  L  G  L  761
GGCCGGGAGGTGGGCGTGGCGGCTGTGGTGCTGGTCCCCATCTTTGCCGCCTTTGCCGTG 2400
 G  R  E  V  G  V  A  A  V  V  L  V  P  I  F  A  A  F  A  V  781
ATGACCGTGGCTATCCTGCTGGTGATGGAGGGACTCTCAGCCTTCCTGCACGCCCTGCGG 2460
 M  T  V  A  I  L  L  V  M  E  G  L  S  A  F  L  H  A  L  R  801
CTGCACTGGGTGGAATTCCAGAACAAGTTCTACTCAGGCACGGGCTACAAGCTGAGTCCC 2520
 L  H  W  V  E  F  Q  N  K  F  Y  S  G  T  G  Y  K  L  S  P  821
TTCACCTTCGCTGCCACAGATGACTAGGGCCCACTGCAGGTCCTGCCAGACCTCCTTCCT 2580
 F                                                             841
GACCTCTGAGGCAGGAGAGGAATAAAGACGGTCCGCCCTGGCAAAAAAAAAAAAAAAAAA 2640
```

FIGURE 1B

```
MG - LFRSEE - - L - QLFL - - - AAY - CVS - L - ELG - V -FRDLN - - V - - FQR -
FV - EVRRCEEMD - - L - F - - EIR - A - - - - - - - - - - - - - - - - P - PROM - - - -
- - E - - - - EL - EI - - NQ - AL - - - - F - - L - - - - - - ILR - - - - - - A - -D - - - E
- - - LL - - - - - G - - - - LR - - - FVAG - I - - - - - - - P - FERMLWR - CRG - - - - - - -
E - E - PLE - PVTGD - - - - - - - F - I - F - GDQ - - - - - V - KI - E - F - - - - YP - - - -
- - - R - - - - - - - - - - - - - DLQ - VL - - TE - - - - - VL - - - - - - - - - - I - V - KM
KAIY - - LN - C - - I - - - T - KCLIAE - WC - V - DL - - - Q - ALR - - - - - - G - - - V - -
I - - - R - - - - - - - - - PPT - TN - FT - - FQ - IVD YGIG - Y - EINPAPYTITFP
FLFAVMFGD - GHG - LM - LFA - - M

US 6,777,537 B1

OSTEOCLAST PROTON PUMP SUBUNIT

RELATED APPLICATION

This application is a continuation of U.S. application Ser. No. 08/605,378, filed Feb. 22, 1996, now abandoned, the entire teachings of which are incorporated herein by reference.

GOVERNMENT FUNDING

Work described herein was supported by NIH grant DE-07378 from the National Institute of Dental Research. The U.S. Government has certain rights in the invention.

BACKGROUND OF THE INVENTION

Solubilization of bone mineral and degradation of the organic matrix of bone depends on the formation, by osteoclasts, of an acidic extracellular compartment.

Osteoclasts are multinucleated giant cells which are responsible for bone resorption and degrade both the inorganic and organic components of bone in a local area subjacent to the matrix attachment site (Blair et al., *J Cell Biol.*, 102:1164–1172 (1986)). Dissolution of the hydroxyapatite mineral phase is dependent upon acidification of the subosteoclastic resorption lacuna, via the action of carbonic anhydrase II and a proton pump (Vaes, *J. Cell Biol.*, 39:676–697 (1968); Baron et al., *J. Cell Biol.*, 101: 2210–2222 (1985); and Blair and Schlesinger, in *Biology and Physiology of the Osteoclast*, Rifkin and Gay, eds. (CRC Press, Boca Raton), pp. 259–287 (1992)).

V-type proton pumps are multi-subunit complexes with two distinct functional domains: a peripherally-associated cytoplasmic catalytic sector that contains 70-(subunit A), 58-(subunit B), 40- and 33-kDa (subunit E) subunits (Xie and Stone, *J. Biol. Chem.*, 263:9859–9866 (1988)), and a proton channel, which is likely composed of 116-, 39-, and 17-kDa components (Crider et al., *J. Biol. Chem.*, 269:17379–17381 (1994)). Considerable speculation has focused on the possibility that osteoclast-specific proton pump subunits exist, particularly because a unique osteoclast mechanism might allow controlled and specific clinical intervention for bone mass disorders such as osteoporosis.

SUMMARY OF THE INVENTION

The present invention pertains to a gene encoding a novel human 116-kDa polypeptide subunit of the osteoclast proton pump (OC-116 KDa). OC-116 KDa mRNA was found at high levels in giant cells of osteoclastomas by Northern analysis but was not detected in tumor stromal cells or in other tissues including kidney, liver, skeletal muscle and brain. OC-116 KDa mRNA was localized to multinucleated giant cells within the osteoclastoma tumor by in situ hybridization. Analysis of the deduced amino acid sequence of the polypeptide indicates that it is a membrane bound protein with at least six transmembrane domains. Thus, it appears that OC-116 kDa represents a novel human 116-kDa subunit of a proton pump which is expressed in osteoclasts in a cell-specific manner. The cell-specific expression of OC-116 KDa makes it useful as a target for therapeutic intervention in diseases with increased resorption of bone or cartilage, such as osteoporosis and osteoarthritis.

Thus, the present invention relates to a gene encoding a polypeptide or protein which is a human osteoclast proton pump subunit. In a particular embodiment, the osteoclast proton pump subunit is a 116-kDa subunit. In another embodiment, the invention also relates to a gene encoding a polypeptide or protein which is an osteoclast proton pump subunit and comprising a nucleotide sequence of SEQ ID NO: 1. The invention described herein also relates to the polypeptide or protein encoded by the described genes. The invention also pertains to isolated DNA encoding a polypeptide which is an osteoclast proton pump subunit and comprising the nucleotide sequence of SEQ ID NO: 1 or its complementary sequence or DNA which hybridizes under conditions of medium to high stringency to the nucleotide sequence of SEQ ID NO: 1 or its complement. The invention further relates to isolated DNA encoding a polypeptide which is a human osteoclast proton pump subunit and which comprises the amino acid sequence of SEQ ID NO: 3 (FIG. 2).

The invention described herein also relates to a novel polypeptide or protein which is a human 116-kDa proton pump subunit. The invention further relates to a polypeptide or protein which is an osteoclast proton pump subunit and has the amino acid sequence of SEQ ID NO: 2. The invention also relates to a polypeptide or protein which is a human proton pump subunit and which comprises the amino acid sequence of SEQ ID NO: 3.

The present invention also relates to antibodies which bind a polypeptide which is a human osteoclast proton pump subunit. For instance, polyclonal and monoclonal antibodies which bind to the described polypeptides or proteins are within the scope of the invention. The invention also pertains to DNA constructs comprising DNA encoding a polypeptide which is an osteoclast proton pump subunit, as well as to host cells stably transformed or transfected with the DNA constructs of this invention.

The present invention also relates to assays for identifying agents which alter the rate of bone degradation. In particular, the agent to be tested is administered to a test subject or added to an in vitro cell culture, and the rate of bone degradation is determined and compared with the rate of bone degradation in a control subject or cell culture which has not been treated with the test agent. An increase or decrease in the rate of bone degradation in the test animal or cell culture indicates that the tested agent alters the rate of bone degradation.

The present invention also relates to methods of treating bone mass disorders characterized by an undesirably high rate of bone degradation, such as osteoporosis and osteoarthritis. In a particular embodiment, an agent which decreases the rate of bone degradation by decreasing the activity of a 116-kDa proton pump subunit (e.g., an antagonist of OC-116 KDa) is administered in a therapeutically appropriate amount to a patient who has a detrimentally increased rate of bone degradation, thereby decreasing the patient's bone degradation rate.

The present invention also relates to methods of treating bone mass disorders characterized by an undesirably low rate of bone degradation. In a particular embodiment, an agent which increases the rate of bone degradation by increasing the activity of a 116-kDa proton pump subunit (e.g., an agonist of OC-116 KDa) is administered in a therapeutically appropriate amount to a patient who has a detrimentally decreased rate of bone degradation, thereby increasing the patient's bone degradation rate. Alternatively, a polypeptide which is a human 116-kDa osteoclast proton pump subunit, optionally formulated with a physiologically appropriate medium, can be administered to a subject with a detrimentally decreased rate of bone degradation. The present invention also pertains to pharmaceutical compositions comprising a polypeptide which is a human 116-kDa osteoclast proton pump subunit, or an agonist or antagonist thereof.

The polypeptides and proteins of the present invention also have utility as osteoclast cell surface markers. Expression of the described polypeptides or proteins is characteristic of osteoclasts, and is unlikely to be found in extracellular fluids such as blood, since the proteins are integral membrane proteins. Thus, these proteins can be labelled, e.g., radioactively or fluorescently, and used as cell surface markers for osteoclasts.

BRIEF DESCRIPTION OF THE DRAWINGS

FIGS. 1A and 1B represent the nucleotide sequence (SEQ ID NO: 1) and deduced amino acid sequence (SEQ ID NO: 2) of human OC-116 KDa.

clastoma cDNA library. The primary structure of the 116-kDa polypeptide predicts a 822-residue protein composed of two large domains, each of which constitutes approximately half of the protein: a highly charged hydrophilic amino-terminal domain and a hydrophobic carboxyl terminal domain that contains multiple membrane-spanning regions. At least six transmembrane regions are present in the carboxyl-terminal half of the OC-116 KDa polypeptide (Table 1), as judged by the criteria of Klein et al. (Klein et al., *Biochem. Biophys. Acta.*, 815:468–476 (1985)) and Kyte and Doolittle (Kyte and Doolittle, *J. Mol. Biol.*, 157:105–132 (1982)).

TABLE 1

| No. | Sequence | Hydrophobicity | Residues |
| --- | --- | --- | --- |
| 1 | YTIITFPFLFAVMFGDVGHGLLMFLFALAMVL<br>SEQ ID NO: 4 | −2.96 | 391–422 |
| 2 | QTFFRGRYLLLLMGLFSIYTGFIYNE<br>SEQ ID NO: 5 | −2.93 | 438–463 |
| 3 | MSVILGVVHMAFGVVLGVFNH<br>SEQ ID NO: 6 | −2.81 | 537–558 |
| 4 | LPELTFLLGLFGYLVFLVIYKWLCVWAARA<br>SEQ ID NO: 7 | −3.14 | 571–600 |
| 5 | QATLVVLALAMVPILLLGTPLHL<br>SEQ ID NO: 8 | −3.34 | 632–653 |
| 6 | EVGVAAVVLVPIFAAFAVMTVAILLVMEGLSAF<br>SEQ ID NO: 9 | −3.46 | 764–796 |

FIG. 2 illustrates the consensus amino acid sequence (SEQ ID NO: 3) resulting from an alignment of the amino acid sequences of human OC-116 KDA, rat and bovine 116-kDa proton pump subunits. Gaps (indicated by dashes) were introduced to maximize alignment of the sequences.

DETAILED DESCRIPTION OF THE INVENTION

Considerable effort has focused on the characterization of the special properties of the osteoclast proton pump. As described herein, a gene encoding a human 116-kDa polypeptide of the vacuolar proton pump, which appears to be uniquely expressed in osteoclast cells, has been isolated.

In order to solubilize bone mineral and degrade the organic matrix of bone, osteoclasts must secrete 1–2 protons for every $Ca^{2+}$ liberated. This transport is a major metabolic activity of osteoclasts and requires an electrogenic proton pump. The proton pump has not been purified in homogeneous form from mammalian osteoclast-ruffled membranes, and therefore its structure and biochemical properties have not yet been described in detail. Based upon immunological cross-reactivity, Blair et al. (Blair et al. (1989)) hypothesized that the osteoclast proton pump is a V-type proton pump. However, the osteoclast proton pump possesses several unique features, including a unique pharmacological profile; that is, the proton pump in osteoclast-derived membranes was not only shown to be sensitive to NEM and Bafilomycin A1, similar to the classical vacuolar proton pump, but also to be sensitive to vanadate, an inhibitor of P-type ATPase (Chattejee et al., *Proc. Natl. Acad. Sci. USA*, 89:6257–6261 (1992)). Furthermore, the osteoclast proton pump is the most active of all acid transport systems studied. Some of these properties may be dependent upon the activity of the OC-116 KDa subunit in osteoclasts.

As described herein, a gene encoding a novel human osteoclast proton pump 116-kDa subunit (OC-116 KDa) has been identified by differential screening of a human osteo- Approximately $12 \times 10^3$ clones from a pcDNAII osteoclastoma library were replica-plated and were screened by differential hybridization using mixed cDNA probes derived by reverse transcription of mRNA from either the original osteoclastoma tumor (osteoclast+) or from propagated stromal cell mRNA (osteoclast−). As described previously (Li et al., *J. Bone Mine. Res.*, 10:1197–1202 (1995)), 195 clones gave a positive hybridization signal with tumor cDNA, but were negative or very weakly positive with stromal cell cDNA. Of these 195 clones, 6 contained a novel human cathepsin (Li et al., 1995), 14 clones contained inserts with a sequence identical to TRAP, and 77 clones encoded MMP-9 (92-kDa type IV collagenase) (Wucherpfennig et al. (1994)), all of which are markers of human osteoclasts.

In addition, one clone which gave a positive hybridization signal with tumor cDNA, but was negative with stromal cell cDNA, was found to possess approximately 60% homology to the rat 116-kDA vacuolar type proton pump subunit, but was not identical to any known proton pump subunit. This clone was designated OC-116 KDa.

Northern analysis of mRNA from the osteoclastoma tumor using an $\alpha^{32}$P-labelled 1.0 kb 3' OC-116 KDa cDNA probe revealed a transcript of approximately 2.7 kb. A 0.5 kb probe from the 5' end of OC-116 kDa gave the same result (data not shown). OC-116 KDa mRNA was found at high levels in the osteoclastoma tumor, and at much lower levels in the human pancreatic adenocarcinoma cell line (AsPC-1), but was not detected in skeletal muscle, liver, kidney, or brain. OC-116 KDa MRNA was also absent from osteoclastoma stromal cells, normal rat osteoblasts (ROB), as well as a panel of human cell lines: osteoblastic (HOS-TE85), myelomonocytic (U-937), T lymphocyte (HSB-2), epithelial (laryngeal carcinoma HEp-2), neuroblastoma (SK-N-MC), and normal skin fibroblasts (CRL 1467).

Rescreening the pcDNAII library failed to yield clones containing full-length inserts. A second library was therefore constructed in phage using the Lambda-ZAP system (Stratagene). This library consisted of ~$6 \times 10^5$ clones of average insert length 1.0 kb. Screening of this library yielded 25 positive clones, of which the two longest (p-18 and p-43) contained inserts of greater than 2.6 kb. Complete bidirectional sequence analysis was carried out on the p-43 clone. Four other clones including p-18 were partially sequenced. All sequences were identical.

The nucleotide sequence (SEQ ID NO: 1) and the deduced amino acid sequence (SEQ ID NO: 2) of the OC-116 KDa cDNA clone are shown in FIGS. 1A and 1B. The nucleotide sequence of the cDNA encoding the OC-116 KDa proton pump polypeptide contains 2622 base pairs excluding the 3'-poly(A) tail. The cDNA contains a 57 base pair 5' untranslated region, and a rather short 3' untranslated region of 99 base pairs. The nucleotide sequence contains an open reading frame, starting from the first ATG codon, encoding an 822-amino acid polypeptide. The sequence context of the putative initiator methionine has a flanking sequence in agreement with the consensus sequences for an initiator methionine (1/G)CCATGG) (Kozak, *Nucleic Acids Res.*, 15:8125–8148 (1987)). At the 3' end, the AATAAA sequence is a common polyadenylation signal. The cDNA is full-length as judged by the fact that its size corresponds well to the message size observed on RNA blots and that it contains an in-frame termination codon 5' to the initiator methionine. In addition, the cDNA sequence exhibits a single large open reading frame, the translation of which predicts the synthesis of an 822-amino acid protein.

Database searches revealed that OC-116 KDa shows 59.4% homology at the nucleotide level with the rat 116-kDa subunit of the clathrin-coated vesicle proton pump and 59.1% homology with the bovine brain 116-kDa subunit vacuolar proton pump. OC-116 KDa exhibits 46.9% and 47.2% homology at the amino acid level with the rat 116 KDa polypeptide and the bovine 116 KDa polypeptide, respectively (Perin et al., *J. Biol. Chem.* 266:3877–3881 (1991); Peng et al., *J. Biol. Chem.* 269:17262–17266 (1994)).

The composition of OC-116 KDa is characterized by an abundance of hydrophilic resides in the first 390 amino acids and a rather hydrophobic region in the following 432 amino acids. Hydrophobicity plots indicate that at least six transmembrane regions are present in the carboxyl-terminal portion of the molecule. The putative transmembrane regions are separated by spacer regions of different length and hydrophilicity (data not shown).

Based on the hydropathy plots, OC-116 KDa shows structural homology with other 116 KDa hydrophobic membrane proteins with transport-related function, including rat- and bovine-116 KDa (Perin et al. (1991)). All three proteins are about 830 amino acids in length and contain six transmembrane domains with a hydrophilic region between domains. FIG. 2 illustrates the consensus sequence obtained when the amino acid sequences of rat and bovine 116 KDa are aligned with the amino acid sequence of OC-116 KDa.

Cells within the osteoclastoma tumor which produce mRNA for OC-116 KDa were identified by in situ hybridization. A digoxygenin-labelled antisense probe was strongly reactive with all multinucleated osteoclasts, but was unreactive with stromal cells. In contrast, the sense probe produced only minimal background staining, which was not localized to any cell type.

Since OC-116 KDa appears to be a subunit of a V-type proton pump, the possibility that this molecule represents the human homolog of the brain-expressed rat and bovine 116 KDa polypeptide was considered. However several lines of evidence argue against this possibility, and instead indicate that OC-116 KDa represents a different gene. First, the structure of the classical 116-kDa subunits of V-type proton pumps are highly conserved. For example, the rat 116 KDa polypeptide is 96.75% similar to the bovine 116 KDa polypeptide at the amino acid level, whereas OC-116 KDa had only about 47% homology to either the rat or bovine 116 KDa polypeptide. Second, the full length mRNA of OC-116 KDa is 2.7 kb, whereas both rat and bovine full length mRNAs for the 116-kDa subunits are 4.1 kb. Compared to rat and bovine 116 KDa cDNAs, which contain a long 3' untranslated region (UTR) of 1321 base pairs, OC-116 KDa contains a rather short 3' untranslated region of 99 base pairs. The functional significance of this difference is unclear at this time. However, the 3' UTR has been found to affect the function of mRNAs in the cytoplasm in several ways. These include localization, control of mRNA stability, and regulation of translation efficiency (Decker and Parker, Current opinion in *Cell Biology*, 7:386–392 (1995)). These differences may constitute part of the molecular basis for the precise regulation of expression of the osteoclast proton pump during the bone remodeling process. Third, OC-116 KDa MRNA was found at high levels in the osteoclastoma tumor but was not detected in other normal human tissues including kidney, brain, liver and skeletal muscle (data not shown). This is in contrast to the ubiquitous distribution of the rat and bovine 116-kDa subunit. Finally, OC-116 KDa MRNA was localized to osteoclasts within the osteoclastoma tumor by in situ hybridization.

Interestingly, the amino acid sequence of OC-116 KDa also exhibits 59% homology with Tj6, which is an immune suppressor and membrane binding protein described in the mouse (Lee et al., *Molecular Immunology*, 27:1137–1144 (1990)). The functional significance of this similarity is currently unclear.

Although the function of the 116-kDa subunit in the V-type proton pump is not definitively established, it appears to be an essential component of the vertebrate pumps (Wucherpfennig et al., *J. Bone Min. Res.*, 9:549–556 (1994)), and is also present in lower unicellular eukaryotes and plants (Parry et al., *J. Biol. Chem.* 264:20025–20032 (1989); and Kane et al., *J. Biol. Chem.* 264:19236–19244 (1989)). In yeast, disruption by mutation of the gene encoding this subunit results conditional lethality at pH values of greater than 6.5 (Kane, *J. Exp. Biol.* 172:93–103 (1992); and Umemoto et al., *J. Biol. Chem.* 266:24526–24532 (1991)). The 17- and 116-kDa subunits are the components of the proton pump that are most hydrophobic (Arai et al., *J. Biol. Chem.*, 263:8796–8802 (1988)). Based on hydrophilicity plots of the amino acid sequence, OC-116 KDa shows structural homology with other 116-kDa proton pump subunits (data not shown) and also contains a large and highly charged amino-terminal domain of unknown function which may interact with the cytoplasmic catalytic sector. These data suggest that the OC-116 KDa polypeptide may be part of the proton-conducting, intramembranous complex of the vacuolar proton pump, and may also play a role in mediating the coupling between ATP hydrolysis by the cytoplasmic 70- and 58-kDa subunits, and proton translocation by the intramembranous subunits, including perhaps its own transmembrane regions (Perin et al. (1991)).

It remains possible that osteoclasts contain two types of proton pumps, one utilizing OC-116 KDa, and the other employing the classical 116-kDa subunit. Several pieces of data argue against this hypothesis. As shown by Chatterjee et al. (Chatterjee et al. (1992)), it is possible to completely inhibit proton transport with various inhibitors (NEM, Bafilomycin and vanadate) used separately, but there is only one $K_m$ for the presence of various concentrations of ATP in preparations of chicken osteoclasts. Second, a polyclonal antibody against the 116-kDa subunit of the clathrin-coated vesicle proton pump, which cross-reacts with the osteoclast proton pump, detects only one protein band at about 100 kDa in Western blots of both the isolated osteoclast and clathrin-coated vesicle proton pumps (Mattsson et al., *J. Biol. Chem.*, 269:24979–24982 (1994)).

Recently, alternative MRNA splicing was shown to generate tissue-specific isoforms of the 116-kDa subunit of the V-type proton pump in bovine brain (Peng et al. (1994)), and of the A subunit in chicken osteoclasts (Hermamdo et al., *PNAS* 92(13):6087–6091 (1995)). However, isoforms result from alternative MRNA splicing of same gene; that is, in the A isoform of the catalytic A subunit of the vacuolar proton pump in chicken osteoclasts, a 72-base pair cassette replaces a 90-base pair cassette present in the classical Al isoform (Hermamdo et al. (1995)). Similarly, two distinct calcitonin receptors characterized from the giant cell tumor of bone differ from each other only by the presence or absence of a predicted 16-amino acid insert in the putative first intracellular domain (Gorn et al., *J. Clin. Invest.*, 95:2680–2691 (1995)).

Taken together, these data demonstrate that OC-116 KDa represents a novel 116-kDa subunit of a proton pump which is distinct from the previously-described 116-kDa subunit, and which is expressed at high levels in osteoclasts.

The present invention relates to a gene encoding a polypeptide or protein which is a human osteoclast proton pump subunit. In a particular embodiment, the osteoclast proton pump subunit is a 116-kDa subunit. In another embodiment, the invention also relates to a gene encoding a polypeptide or protein which is an osteoclast proton pump subunit and comprising a nucleotide sequence consisting of SEQ ID NO: 1; the invention described herein also relates to the polypeptide or protein encoded by the described genes. The invention also pertains to isolated DNA encoding a polypeptide which is an osteoclast proton pump subunit and comprising the nucleotide sequence of SEQ ID NO: 1 or its complementary sequence or DNA which hybridizes under conditions of medium to high stringency to the nucleotide sequence of SEQ ID NO: 1 or its complement. Stringency conditions which are appropriately termed "medium stringency" or "high stringency" are known to those skilled in the art or can be found in standard texts such as *Current Protocols in Molecular Biology*, John Wiley & Sons, N.Y. (1989), 6.3.1–6.3.6.

The invention described herein also relates to a polypeptide or protein which is a human osteoclast proton pump subunit; in a particular embodiment, the polypeptide or protein is a 116-kDa proton pump subunit. In one embodiment, the polypeptide or protein which is an osteoclast proton pump subunit has the amino acid sequence of SEQ ID NO: 2.

The present invention also relates to antibodies which bind a polypeptide which is an osteoclast proton pump subunit. For instance, polyclonal and monoclonal antibodies which bind to the described polypeptide or protein are within the scope of the invention. A mammal, such as a mouse, hamster or rabbit, can be immunized with an immunogenic form of the polypeptide (i.e., an antigenic fragment of the polypeptide which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)).

The invention also provides expression vectors containing a nucleic acid sequence encoding a polypeptide which is a human osteoclast proton pump subunit operably linked to at least one regulatory sequence. "Operably linked" is intended to meant that the nucleotide sequence is linked to a regulatory sequence in a manner which allow expression of the nucleic acid sequence. Regulatory sequences are art-recognized and are selected to produce a polypeptide which is a human 116-kDa osteoclast proton pump subunit. Accordingly, the term "regulatory sequence" includes promoters, enhancers, and other expression control elements which are described in Goeddel, *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17).

Prokaryotic and eukaryotic host cells transfected by the described vectors are also provided by this invention. For instance, cells which can be transfected with the vectors of the present invention include, but are not limited to, bacterial cells such as *E. coli*, insect cells (baculovirus), yeast or mammalian cells such as Chinese hamster ovary cells (CHO).

Thus, a nucleotide sequence derived from the cloning of the osteoclast proton pump subunit polypeptides described herein can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well known proteins. Similar procedures, or modifications thereof, can be employed to prepare recombinant proteins according to the present invention by microbial means or tissue-culture technology.

The present invention further relates to assays for identifying agents which alter the rate of bone degradation. As used herein, "alters" is intended to mean either increases or decreases. Also as used herein, an "agent" is intended to include, but is not limited to, peptides, drugs and small organic molecules. In particular, the agent to be tested is administered to a test animal or added to an in vitro cell culture, and the rate of bone degradation is determined and compared with the rate of bone degradation in a control animal or cell culture which has not been treated with the test agent. An increase or decrease in the rate of bone degradation in the test animal or cell culture indicates that the agent alters the rate of bone degradation. Thus, the present invention also pertains to agonists and antagonists of the OC-116 KDa protein.

The present invention also relates to methods of treating bone mass disorders such as osteoporosis and osteoarthritis. In a particular embodiment, an agent which decreases the rate of bone degradation (e.g., an antagonist of OC-116 KDa) is administered in a therapeutically appropriate amount to a patient who has a detrimentally increased rate of bone degradation, thereby decreasing the patient's bone degradation rate.

The present invention also relates to methods of treating bone mass disorders characterized by an undesirably low rate of bone degradation. In a particular embodiment, an agent which increases the rate of bone degradation by increasing the activity of a 116-kDa proton pump subunit (e.g., an agonist of OC-116 KDa) is administered in a therapeutically appropriate amount to a patient who has a detrimentally decreased rate of bone degradation, thereby increasing the patient's bone degradation rate. Alternatively, a polypeptide which is a human 116-kDa osteoclast proton pump subunit, optionally formulated with a physiologically appropriate medium, can be administered to a subject with a detrimentally decreased rate of bone degradation.

The present invention also pertains to pharmaceutical compositions comprising a polypeptide which is a human 116-kDa osteoclast proton pump subunit, or an agonist or antagonist thereof. For instance, the polypeptide or protein of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous human osteoclast proton pump subunit polypeptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents.

The polypeptides and proteins of the present invention also have utility as osteoclast cell surface markers. Expression of the described polypeptides is characteristic of osteoclasts, and is unlikely to be found in extracellular fluids such as blood, since the proteins are integral membrane proteins. Thus, these proteins can be labelled, e.g., radioactively or fluorescently, and used as cell surface markers for osteoclasts.

As used herein, terms are understood to have their art-recognized meaning unless otherwise defined. The teachings of references cited herein are hereby incorporated herein by reference.

The invention will be further illustrated by the following non-limiting exemplifications:

EXAMPLES

Cells and Cell Culture

Human osteoclastoma tumors, consisting of ~30% multi-nucleated tartrate resistant acid phosphatase positive (TRAP+) giant cells, were obtained courtesy of Dr. Andrew Rosenberg, Massachusetts General Hospital, Boston, Mass. These multinucleated cells possess a closely similar phenotype to osteoclasts and are also capable of excavating resorption pits on bone slices (Horton and Helfrich, in *Biology and Physiology of the Osteoclast*, Rifkin and Gay, eds. (CRC Press, Boca Raton), pp. 33–53 (1992); and Flanagan et al., *Cancer*, 62:1139–1145 (1988)). The remainder of the tumor consists of "stromal" cells, a mixture of cells types with fibroblastic/mesenchymal morphology. The osteoclastoma tumor was dissociated by a brief trypsinization and was placed into tissue culture in medium consisting of Dulbecco's Minimal Essential Medium. Disaggregated tumor cells were passaged weekly for 4 weeks, at which time all multinucleated, TRAP+ cells had disappeared, while the stromal cells continued to proliferate. Stromal cells were mononuclear, TRAP–, and variably alkaline phosphatase+.

Osteoblastic (HOS-TE85), myelomonocytic (U-937), T lymphocyte (HSB-2), neuroblastoma (SK-N-MC), pancreatic adenocarcinoma (AsPC-1) and normal skin fibroblast (CRL 1467) cell lines were purchased from ATCC, Bethesda, Md. The epithelial cell line Hep-2 was kindly provided by Dr. Margaret Duncan, Forsyth Dental Center. Normal rat osteoblasts (ROB) were obtained by sequential enzymatic digestion of fetal rat calvaria as described in Li et al. (Li et al., *Nucleic Acids Research*, 23:5064–5072 (1995)).

Library Construction and Differential Screening

Two human osteoclastoma cDNA libraries were prepared in pcDNAII vector (InVitrogen) and in the Lambda-ZAP system (Stratagene), and differential screening was performed as described in Li et al. (1995). Briefly, clones were randomly picked from the pcDNAII library and were hand plated in triplicate on nitrocellulose filters. Mixed cDNA probes were produced from MRNA isolated from the osteoclastoma tumor and from propagated stromal cells. The clones which were reactive with the tumor probe, but which were unreactive or only weakly reactive with the stromal cell probe were isolated. Purified DNA from these clones was rescreened in a dot blot format to confirm the original result.

cDNA Cloning and Sequencing

For full-length cDNA characterization, a 1.0 kb putative proton pump probe labelled with $\alpha^{32}$PdCTP was used to screen the Lambda-ZAP osteoclastoma library. Positive clones were purified, and the size of inserts was determined following excision with Kpnl and Xbal. A clone containing a full-length insert of 2.6 kb was subjected to controlled digestion with ExoIII to generate a series of diminishing insert sizes. Sequence analysis was then carried out from both ends by the dideoxy method (Sanger et al., *Proc. Natl. Acad. Sci. USA*, 74: 5463–5467 (1977)) using the Sequenase kit (U.S. Biochemical Corp). Homologies were compared with known proton pump sequences using the BLAST program at the National Center for Biotechnology Information (N. C. B. I.)

Northern Blotting

Total RNA from osteoclastomas and cell lines was isolated by the method of Chomczynski and Sacchi (Chomczynski and Sacchi, *Analytical Biochemistry*, 162(1): 156–159 (1987)). Whole cell RNA from human tissues was purchased from Clontech, Palto Alto, Calif. Total cellular RNA was separated on a 1.0% agarose gel containing 6% formamide and transferred to nylon membranes. The integrity and quality of RNA was confirmed by ethidium bromide staining. Both 1.0 kb 3'-end and 0.5 kb 5'-end OC-116 KDa cDNAs were used as probes. Probes were radiolabeled with $\alpha^{32}$pdCTP using a random primer labeling kit (Stratagene). Hybridization was performed as described previously in Li et al. (1995).

In situ Hybridization

In situ hybridization was performed as described in Li et al. (1995). Briefly, the 1.0 kb OC-116 KDa insert was subcloned into pBluescript SK, and CDNA probes were generated from the T3 (sense) and T7 (antisense) promoters respectively. Probes were labelled with digoxygenin-UTP using the Genius System (Boehringer Mannheim) and developed with an alkaline phosphatase-labelled antibody. In situ hybridization was carried out on 7 mm cryostat sections of a human osteoclastoma. Hybridized probes were visualized immunologically with a digoxygenin-nucleic acid detection kit according to the manufacturer's instructions (Genius System, Boehringer Mannheim). Developed slides were photographed using a Nikon Diaphot microscope.

Equivalents

Those skilled in the art will recognize or be able to ascertain, using no more than routine experimentation, many equivalents to the specific embodiments of the invention described herein. Such equivalents are intended to be encompassed in the scope of the following claims.

SEQUENCE LISTING

<160> NUMBER OF SEQ ID NOS: 9

<210> SEQ ID NO 1
<211> LENGTH: 2640
<212> TYPE: DNA
<213> ORGANISM: Homo sapiens

<400> SEQUENCE: 1

```
cggcgtgcgc ggacgggcag ccagcagcgg aggcgcggcg cagcacaccc ggggaccatg      60
ggctccatgt tccggagcga ggaggtggcc ctggtccagc tctttctgcc cacagcggct     120
gcctacacct gcgtgagtcg gctgggcgag ctgggcctcg tggagttcag agacctcaac     180
gcctcggtga gcgccttcca gagacgcttt gtggttgatg tttggcgctg tgaggagctg     240
gagaagacct tcaccttcct gcaggaggag gtgcggcggg ctgggctggt cctgcccccg     300
ccaaagggga ggctgccggc acccccaccc cgggacctgc tgcgcatcca ggaggagacg     360
gagcgcctgg cccaggagct gcgggatgtg cggggcaacc agcaggccct gcgggcccag     420
ctgcaccagc tgcagctcca cgccgccgtg ctacgccagg gccatgaacc tcagctggca     480
gccgcccaca cagatggggc ctcagagagg acgcccctgc tccaggcccc cggggggccg     540
caccaggacc tgagggtcaa ctttgtggca ggtgccgtgg agcccacaa ggcccctgcc     600 ctagagcgcc tgctctggag ggcctgccgc ggcttcctca ttgccagctt cagggagctg     660
gagcagccgc tggagcaccc cgtgacgggc gagccagcca cgtggatgac cttcctcatc     720
tcctactggg gtgagcagat cggacagaag atccgcaaga tcacggactg cttccactgc     780
cacgtcttcc cgtttctgca gcaggaggag gcccgcctcg gggccctgca gcagctgcaa     840
cagcagagcc aggagctgca ggaggtcctc ggggagacag agcggttcct gagccaggtg     900
ctaggccggg tgctgcagct gctgccgcca gggcaggtgc aggtccacaa gatgaaggcc     960
gtgtacctgg ccctgaacca gtgcagcgtg agcaccacgc acaagtgcct cattgccgag    1020
gcctggtgct ctgtgcgaga cctgcccgcc ctgcaggagg cctgcgggga cagctcgatg    1080
gaggagggag tgagtgccgt ggctcaccgc atcccctgcc gggacatgcc ccccacactc    1140
atccgcacca accgcttcac ggccagcttc cagggcatcg tggatcgcta cggcgtgggc    1200
cgctaccagg aggtcaaccc cgctccctac accatcatca ccttcccctt cctgtttgct    1260
gtgatgttcg gggatgtggg ccacgggctg ctcatgttcc tcttcgccct ggccatggtc    1320
cttgcggaga accgaccggc tgtgaaagcc gcgcagaacg agatctggca gactttcttc    1380
aggggccgct acctgctcct gcttatgggc ctgttctcca tctacaccgg cttcatctac    1440
aacgagtgct tcagtcgcgc caccagcatc ttcccctcgg gctggagtgt ggccgccatg    1500
gccaaccagt ctgctggag tgatgcattc ctgcccagc acacgatgct tacccctggat    1560 cccaacgtca ccggtgtctt cctgggaccc tacccctttg gcatcgatcc tatttggagc    1620
```

-continued

```
ctggctgcca accacttgag cttcctcaac tccttcaaga tgaagatgtc cgtcatcctg    1680
ggcgtcgtgc acatggcctt tggggtggtc ctcggagtct tcaaccacgt gcactttggc    1740
cagaggcacc ggctgctgct ggagacgctg ccggagctca ccttcctgct gggactcttc    1800
ggttacctcg tgttcctagt catctacaag tggctgtgtg tctgggctgc cagggccgcc    1860
tcgcccagca tcctcatcca cttcatcaac atgttcctct ctcccacag ccccagcaac     1920 aggctgctct accccggca ggaggtggtc caggccacgc tggtggtcct ggccttggcc     1980
atggtgccca tcctgctgct ggcacaccc ctgcacctgc tgcaccgcca ccgccgccgc     2040
ctgcggagga ggcccgctga ccgacaggag gaaaacaagg ccgggttgct ggacctgcct    2100
gacgcatctg tgaatggctg gagctccgat gaggaaaagg caggggggcct ggatgatgaa   2160 gaggaggccg agctcgtccc ctccgaggtg ctcatgcacc aggccatcca caccatcgag    2220
ttctgcctgg gctgcgtctc caacaccgcc tcctacctgc gcctgtgggc cctgagcctg    2280
gcccacgccc agctgtccga ggttctgtgg gccatggtga tgcgcatagg cctgggcctg    2340
ggccgggagg tgggcgtggc ggctgtggtg ctggtcccca tctttgccgc ctttgccgtg    2400
atgaccgtgg ctatcctgct ggtgatggag ggactctcag ccttcctgca cgccctgcgg    2460
ctgcactggg tggaattcca gaacaagttc tactcaggca cgggctacaa gctgagtccc    2520
ttcaccttcg ctgccacaga tgactagggc ccactgcagg tcctgccaga cctccttcct    2580
gacctctgag gcaggagagg aataaagacg gtccgccctg caaaaaaaa aaaaaaaaa     2640
```

<210> SEQ ID NO 2
<211> LENGTH: 822
<212> TYPE: PRT
<213> ORGANISM: Homo sapiens

<400> SEQUENCE: 2

```
Met Gly Ser Met Phe Arg Ser Glu Glu Val Ala Leu Val Gln Leu Phe
  1               5                  10                  15

Leu Pro Thr Ala Ala Ala Tyr Thr Cys Val Ser Arg Leu Gly Glu Leu
             20                  25                  30

Gly Leu Val Glu Phe Arg Asp Leu Asn Ala Ser Val Ser Ala Phe Gln
         35                  40                  45

Arg Arg Phe Val Val Asp Val Trp Arg Cys Glu Leu Glu Lys Thr
     50                  55                  60

Phe Thr Phe Leu Gln Glu Val Arg Ala Gly Leu Val Leu Pro
 65                  70                  75                  80

Pro Pro Lys Gly Arg Leu Pro Ala Pro Pro Arg Asp Leu Leu Arg
                 85                  90                  95

Ile Gln Glu Glu Thr Glu Arg Leu Ala Gln Glu Leu Arg Asp Val Arg
                100                 105                 110

Gly Asn Gln Gln Ala Leu Arg Ala Gln Leu His Gln Leu Gln Leu His
            115                 120                 125

Ala Ala Val Leu Arg Gln Gly His Glu Pro Gln Leu Ala Ala Ala His
        130                 135                 140

Thr Asp Gly Ala Ser Glu Arg Thr Pro Leu Leu Gln Ala Pro Gly Gly
145                 150                 155                 160

Pro His Gln Asp Leu Arg Val Asn Phe Val Ala Gly Ala Val Glu Pro
                165                 170                 175

His Lys Ala Pro Ala Leu Glu Arg Leu Leu Trp Arg Ala Cys Arg Gly
            180                 185                 190
```

```
Phe Leu Ile Ala Ser Phe Arg Glu Leu Glu Gln Pro Leu Glu His Pro
        195                 200                 205

Val Thr Gly Glu Pro Ala Thr Trp Met Thr Phe Leu Ile Ser Tyr Trp
    210                 215                 220

Gly Glu Gln Ile Gly Gln Lys Ile Arg Lys Ile Thr Asp Cys Phe His
225                 230                 235                 240

Cys His Val Phe Pro Phe Leu Gln Gln Glu Ala Arg Leu Gly Ala
                245                 250                 255

Leu Gln Gln Leu Gln Gln Ser Gln Glu Leu Gln Glu Val Leu Gly
            260                 265                 270

Glu Thr Glu Arg Phe Leu Ser Gln Val Leu Gly Arg Val Leu Gln Leu
        275                 280                 285

Leu Pro Pro Gly Gln Val Gln Val His Lys Met Lys Ala Val Tyr Leu
        290                 295                 300

Ala Leu Asn Gln Cys Ser Val Ser Thr Thr His Lys Cys Leu Ile Ala
305                 310                 315                 320

Glu Ala Trp Cys Ser Val Arg Asp Leu Pro Ala Leu Gln Glu Ala Leu
                325                 330                 335

Arg Asp Ser Ser Met Glu Glu Gly Val Ser Ala Val Ala His Arg Ile
            340                 345                 350

Pro Cys Arg Asp Met Pro Pro Thr Leu Ile Arg Thr Asn Arg Phe Thr
        355                 360                 365

Ala Ser Phe Gln Gly Ile Val Asp Arg Tyr Gly Val Gly Arg Tyr Gln
        370                 375                 380

Glu Val Asn Pro Ala Pro Tyr Thr Ile Ile Thr Phe Pro Phe Leu Phe
385                 390                 395                 400

Ala Val Met Phe Gly Asp Val Gly His Gly Leu Leu Met Phe Leu Phe
                405                 410                 415

Ala Leu Ala Met Val Leu Ala Glu Asn Arg Pro Ala Val Lys Ala Ala
            420                 425                 430

Gln Asn Glu Ile Trp Gln Thr Phe Phe Arg Gly Arg Tyr Leu Leu Leu
        435                 440                 445

Leu Met Gly Leu Phe Ser Ile Tyr Thr Gly Phe Ile Tyr Asn Glu Cys
    450                 455                 460

Phe Ser Arg Ala Thr Ser Ile Phe Pro Ser Gly Trp Ser Val Ala Ala
465                 470                 475                 480

Met Ala Asn Gln Ser Gly Trp Ser Asp Ala Phe Leu Ala Gln His Thr
                485                 490                 495

Met Leu Thr Leu Asp Pro Asn Val Thr Gly Val Phe Leu Gly Pro Tyr
            500                 505                 510

Pro Phe Gly Ile Asp Pro Ile Trp Ser Leu Ala Ala Asn His Leu Ser
        515                 520                 525

Phe Leu Asn Ser Phe Lys Met Lys Met Ser Val Ile Leu Gly Val Val
        530                 535                 540

His Met Ala Phe Gly Val Val Leu Gly Val Phe Asn His Val His Phe
545                 550                 555                 560

Gly Gln Arg His Arg Leu Leu Leu Glu Thr Leu Pro Glu Leu Thr Phe
                565                 570                 575

Leu Leu Gly Leu Phe Gly Tyr Leu Val Phe Leu Val Ile Tyr Lys Trp
            580                 585                 590

Leu Cys Val Trp Ala Ala Arg Ala Ala Ser Pro Ser Ile Leu Ile His
        595                 600                 605

Phe Ile Asn Met Phe Leu Phe Ser His Ser Pro Ser Asn Arg Leu Leu
```

-continued

```
                610                 615                 620
Tyr Pro Arg Gln Glu Val Val Gln Ala Thr Leu Val Val Leu Ala Leu
625                 630                 635                 640

Ala Met Val Pro Ile Leu Leu Leu Gly Thr Pro Leu His Leu Leu His
                645                 650                 655

Arg His Arg Arg Arg Leu Arg Arg Pro Ala Asp Arg Gln Glu Glu
            660                 665                 670

Asn Lys Ala Gly Leu Leu Asp Leu Pro Asp Ala Ser Val Asn Gly Trp
            675                 680                 685

Ser Ser Asp Glu Glu Lys Ala Gly Gly Leu Asp Glu Glu Glu Ala
            690                 695                 700

Glu Leu Val Pro Ser Glu Val Leu Met His Gln Ala Ile His Thr Ile
705                 710                 715                 720

Glu Phe Cys Leu Gly Cys Val Ser Asn Thr Ala Ser Tyr Leu Arg Leu
                725                 730                 735

Trp Ala Leu Ser Leu Ala His Ala Gln Leu Ser Glu Val Leu Trp Ala
                740                 745                 750

Met Val Met Arg Ile Gly Leu Gly Leu Gly Arg Glu Val Gly Val Ala
            755                 760                 765

Ala Val Val Leu Val Pro Ile Phe Ala Ala Phe Ala Val Met Thr Val
770                 775                 780

Ala Ile Leu Leu Val Met Glu Gly Leu Ser Ala Phe Leu His Ala Leu
785                 790                 795                 800

Arg Leu His Trp Val Glu Phe Gln Asn Lys Phe Tyr Ser Gly Thr Gly
                805                 810                 815

Tyr Lys Leu Ser Pro Phe
            820

<210> SEQ ID NO 3
<211> LENGTH: 847
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(847)
<223> OTHER INFORMATION: Xaa = Any Amino Acid

<400> SEQUENCE: 3

Met Gly Xaa Leu Phe Arg Ser Glu Glu Xaa Xaa Leu Xaa Gln Leu Phe
  1               5                  10                  15

Leu Xaa Xaa Xaa Ala Ala Tyr Xaa Cys Val Ser Xaa Leu Xaa Glu Leu
            20                  25                  30

Gly Xaa Val Xaa Phe Arg Asp Leu Asn Xaa Xaa Val Xaa Xaa Phe Gln
        35                  40                  45

Arg Xaa Phe Val Xaa Glu Val Arg Arg Cys Glu Glu Met Asp Xaa Xaa
    50                  55                  60

Leu Xaa Phe Xaa Xaa Xaa Glu Ile Arg Xaa Ala Xaa Xaa Xaa Xaa Xaa
65                  70                  75                  80

Xaa Xaa Xaa Xaa Xaa Xaa Xaa Pro Xaa Pro Arg Asp Met Xaa Xaa
            85                  90                  95

Xaa Xaa Xaa Xaa Glu Xaa Xaa Xaa Glu Leu Xaa Glu Ile Xaa
        100                 105                 110

Xaa Asn Gln Xaa Ala Leu Xaa Xaa Xaa Phe Xaa Xaa Leu Xaa Xaa Xaa
    115                 120                 125
```

-continued

Xaa Xaa Ile Leu Arg Xaa Xaa Xaa Xaa Xaa Xaa Xaa Ala Xaa
    130                 135             140

Xaa Asp Xaa Xaa Xaa Glu Xaa Xaa Leu Leu Xaa Xaa Xaa Xaa
145             150             155             160

Gly Xaa Xaa Xaa Xaa Leu Arg Xaa Xaa Phe Val Ala Gly Xaa Ile Xaa
            165             170             175

Xaa Xaa Xaa Xaa Pro Xaa Phe Glu Arg Met Leu Trp Arg Xaa Cys Arg
            180             185             190

Gly Xaa Xaa Xaa Xaa Xaa Xaa Glu Xaa Glu Xaa Pro Leu Glu Xaa
        195             200             205

Pro Val Thr Gly Asp Xaa Xaa Xaa Xaa Xaa Phe Xaa Ile Xaa Phe
    210             215             220

Xaa Gly Asp Gln Xaa Xaa Xaa Xaa Val Xaa Lys Ile Xaa Glu Xaa Phe
225             230             235             240

Xaa Xaa Xaa Xaa Tyr Pro Xaa Xaa Xaa Xaa Xaa Xaa Arg Xaa Xaa
            245             250             255

Xaa Xaa Xaa Xaa Xaa Xaa Xaa Xaa Asp Leu Gln Xaa Val Leu
            260             265             270

Xaa Xaa Thr Glu Xaa Xaa Xaa Xaa Xaa Val Leu Xaa Xaa Xaa Xaa
        275             280             285

Xaa Xaa Xaa Xaa Xaa Xaa Ile Xaa Val Xaa Lys Met Lys Ala Ile Tyr
        290             295             300

Xaa Xaa Leu Asn Xaa Cys Xaa Ile Xaa Xaa Thr Xaa Lys Cys Leu Ile
305             310             315             320

Ala Glu Xaa Trp Cys Xaa Val Xaa Asp Leu Xaa Xaa Xaa Gln Xaa Ala
            325             330             335

Leu Arg Xaa Xaa Xaa Xaa Xaa Xaa Gly Xaa Xaa Val Xaa Xaa Ile Xaa
            340             345             350

Xaa Arg Xaa Xaa Xaa Xaa Xaa Xaa Pro Pro Thr Xaa Xaa Xaa Thr Asn
        355             360             365

Xaa Phe Thr Xaa Xaa Phe Gln Xaa Ile Val Asp Tyr Gly Ile Gly Xaa
        370             375             380

Tyr Xaa Glu Ile Asn Pro Ala Pro Tyr Thr Ile Ile Thr Phe Pro Phe
385             390             395             400

Leu Phe Ala Val Met Phe Gly Asp Xaa Gly His Gly Xaa Leu Met Xaa
                405             410             415

Leu Phe Ala Xaa Xaa Met Val Leu Xaa Glu Xaa Arg Xaa Xaa Xaa Xaa
            420             425             430

Xaa Xaa Xaa Asn Glu Xaa Phe Xaa Xaa Xaa Phe Xaa Gly Arg Tyr Xaa
        435             440             445

Xaa Leu Leu Met Gly Xaa Phe Ser Ile Tyr Thr Gly Leu Ile Tyr Asn
    450             455             460

Asp Cys Phe Ser Xaa Xaa Xaa Xaa Ile Phe Xaa Ser Xaa Trp Ser Val
465             470             475             480

Xaa Xaa Met Xaa Xaa Xaa Xaa Xaa Trp Xaa Glu Xaa Xaa Leu Xaa Xaa
        485             490             495

Xaa Xaa Xaa Leu Xaa Leu Xaa Pro Xaa Val Xaa Gly Val Phe Xaa Gly
            500             505             510

Pro Tyr Pro Phe Gly Ile Asp Pro Ile Trp Xaa Ala Xaa Asn Xaa
    515             520             525

Leu Xaa Phe Leu Asn Ser Phe Lys Met Lys Met Ser Val Ile Leu Gly
    530             535             540

Ile Ile His Met Xaa Phe Gly Val Xaa Leu Xaa Xaa Phe Asn His Xaa

-continued

```
                545                 550                 555                 560
Xaa Phe Xaa Xaa Xaa Xaa Xaa Xaa Phe Xaa Xaa Pro Glu Xaa
                    565                 570                 575

Xaa Phe Met Xaa Xaa Leu Phe Gly Tyr Leu Val Xaa Leu Ile Xaa Tyr
                580                 585                 590

Lys Trp Xaa Xaa Xaa Tyr Xaa Ala Xaa Xaa Xaa Xaa Xaa Pro Ser
            595                 600                 605

Xaa Leu Ile His Phe Ile Asn Asn Phe Leu Phe Ser Xaa Xaa Xaa Ser
        610                 615                 620

Xaa Asn Xaa Met Leu Tyr Xaa Xaa Gln Xaa Xaa Ile Gln Xaa Xaa Leu
625                 630                 635                 640

Val Val Xaa Ala Leu Xaa Xaa Val Pro Xaa Met Leu Leu Xaa Xaa Pro
                645                 650                 655

Leu Xaa Leu Xaa Xaa Xaa Xaa Arg Xaa Xaa Xaa Xaa Xaa Xaa
                660                 665                 670

Xaa Xaa Xaa Xaa Xaa Arg Xaa Xaa Xaa Xaa Xaa Phe Xaa Xaa Ala
            675                 680                 685

Xaa Xaa Xaa Xaa Xaa Xaa Xaa Xaa Xaa Xaa Xaa Ser Xaa Xaa
        690                 695                 700

Xaa Glu Xaa Ala Xaa Xaa Xaa Xaa Glu Asp Glu Xaa Xaa Asp Phe Xaa
705                 710                 715                 720

Xaa Xaa Asp Xaa Met Xaa His Gln Ala Ile His Thr Ile Glu Tyr Cys
            725                 730                 735

Leu Gly Cys Ile Ser Asn Thr Ala Ser Tyr Leu Arg Leu Trp Ala Leu
                740                 745                 750

Ser Leu Ala His Ala Gln Leu Ser Glu Val Leu Trp Xaa Met Val Xaa
                755                 760                 765

Xaa Ile Gly Leu Xaa Xaa Xaa Xaa Xaa Gly Xaa Xaa Xaa Xaa Xaa
            770                 775                 780

Phe Xaa Xaa Ile Phe Ala Ala Phe Ala Xaa Leu Thr Val Ala Ile Leu
785                 790                 795                 800

Leu Ile Met Glu Gly Leu Ser Ala Phe Leu His Ala Leu Arg Leu His
                805                 810                 815

Trp Val Glu Phe Gln Asn Lys Phe Tyr Xaa Gly Thr Gly Phe Lys Phe
                820                 825                 830

Xaa Pro Pro Xaa Xaa Xaa Xaa Xaa Xaa Xaa Xaa Xaa Xaa
            835                 840                 845

<210> SEQ ID NO 4
<211> LENGTH: 32
<212> TYPE: PRT
<213> ORGANISM: Homo sapiens

<400> SEQUENCE: 4

Tyr Thr Ile Ile Thr Phe Pro Phe Leu Phe Ala Val Met Phe Gly Asp
 1               5                  10                  15

Val Gly His Gly Leu Leu Met Phe Leu Phe Ala Leu Ala Met Val Leu
                20                  25                  30

<210> SEQ ID NO 5
<211> LENGTH: 26
<212> TYPE: PRT
<213> ORGANISM: Homo sapiens

<400> SEQUENCE: 5

Gln Thr Phe Phe Arg Gly Arg Tyr Leu Leu Leu Leu Met Gly Leu Phe
```

-continued

```
                1               5                    10                  15
Ser Ile Tyr Thr Gly Phe Ile Tyr Asn Glu
                20                  25

<210> SEQ ID NO 6
<211> LENGTH: 21
<212> TYPE: PRT
<213> ORGANISM: Homo sapiens

<400> SEQUENCE: 6

Met Ser Val Ile Leu Gly Val Val His Met Ala Phe Gly Val Val Leu
 1               5                  10                  15

Gly Val Phe Asn His
            20

<210> SEQ ID NO 7
<211> LENGTH: 30
<212> TYPE: PRT
<213> ORGANISM: Homo sapiens

<400> SEQUENCE: 7

Leu Pro Glu Leu Thr Phe Leu Leu Gly Leu Phe Gly Tyr Leu Val Phe
 1               5                  10                  15

Leu Val Ile Tyr Lys Trp Leu Cys Val Trp Ala Ala Arg Ala
            20                  25                  30

<210> SEQ ID NO 8
<211> LENGTH: 23
<212> TYPE: PRT
<213> ORGANISM: Homo sapiens

<400> SEQUENCE: 8

Gln Ala Thr Leu Val Val Leu Ala Leu Ala Met Val Pro Ile Leu Leu
 1               5                  10                  15

Leu Gly Thr Pro Leu His Leu
            20

<210> SEQ ID NO 9
<211> LENGTH: 33
<212> TYPE: PRT
<213> ORGANISM: Homo sapiens

<400> SEQUENCE: 9

Glu Val Gly Val Ala Ala Val Val Leu Val Pro Ile Phe Ala Ala Phe
 1               5                  10                  15

Ala Val Met Thr Val Ala Ile Leu Leu Val Met Glu Gly Leu Ser Ala
            20                  25                  30

Phe
```

The invention claimed is:

1. An isolated polypeptide encoded by an isolated DNA comprising a nucleotide sequence of SEQ ID NO: 1.

2. An isolated polypeptide comprising the amino acid sequence of SEQ ID NO: 2.

* * * * *